US012648991B2

(12) United States Patent (10) Patent No.: US 12,648,991 B2
LaFleur et al. (45) Date of Patent: Jun. 9, 2026

(54) ORAL RESPIRATORY VACCINE

(71) Applicant: Intervet Inc., Madison, NJ (US)

(72) Inventors: Rhonda L. LaFleur, Omaha, NE (US); Jennifer C. Dant, Elkhorn, NE (US); Ian Tarpey, St. Ives (GB); Zhichang Xu, Omaha, NE (US)

(73) Assignee: Intervet Inc., Rahway, NJ (US)

( * ) Notice: Subject to any disclaimer, the term of this patent is extended or adjusted under 35 U.S.C. 154(b) by 812 days.

(21) Appl. No.: 17/783,228

(22) PCT Filed: Dec. 17, 2020

(86) PCT No.: PCT/EP2020/086683
§ 371 (c)(1),
(2) Date: Jun. 7, 2022

(87) PCT Pub. No.: WO2021/122928
PCT Pub. Date: Jun. 24, 2021

(65) Prior Publication Data
US 2023/0012140 A1 Jan. 12, 2023

Related U.S. Application Data

(60) Provisional application No. 62/949,928, filed on Dec. 18, 2019.

(51) Int. Cl.
*A61K 39/155* (2006.01)
*A61K 39/02* (2006.01)
*A61P 31/04* (2006.01)
*A61P 31/14* (2006.01)
*A61K 39/00* (2006.01)

(52) U.S. Cl.
CPC .......... *A61K 39/155* (2013.01); *A61K 39/099* (2013.01); *A61P 31/04* (2018.01); *A61P 31/14* (2018.01); *A61K 2039/522* (2013.01); *A61K 2039/5254* (2013.01); *A61K 2039/54* (2013.01); *A61K 2039/545* (2013.01); *A61K 2039/552* (2013.01); *A61K 2039/70* (2013.01); *C12N 2760/18734* (2013.01)

(58) Field of Classification Search
CPC ............ A61K 39/155; A61K 2039/552; A61K 39/099; A61P 31/14; A61P 31/04
See application file for complete search history.

(56) References Cited

U.S. PATENT DOCUMENTS

| | | | |
|---|---|---|---|
| 6,177,082 B1 | 1/2001 | Dowling et al. | |
| 8,414,901 B2 * | 4/2013 | Callister | ............ A61K 39/0225 |
| | | | 424/234.1 |
| 8,821,852 B2 * | 9/2014 | O'Connell | .............. A61P 31/04 |
| | | | 424/93.4 |
| 11,141,545 B2 | 10/2021 | Anderson et al. | |
| 11,883,476 B2 * | 1/2024 | LaFleur | .................. A61P 31/04 |
| 2018/0154090 A1 | 6/2018 | Anderson et al. | |
| 2020/0316192 A1 | 10/2020 | Tucker et al. | |

FOREIGN PATENT DOCUMENTS

| | | | | |
|---|---|---|---|---|
| AU | 2019204604 A1 * | 7/2019 | | |
| CN | 1835767 A | 9/2006 | | |
| CN | 104411330 A | 3/2015 | | |
| EP | 2129392 B1 | 7/2013 | | |
| EP | 2762163 B1 | 1/2018 | | |
| EP | 3300743 A1 | 4/2018 | | |
| JP | 2008169207 A | 7/2008 | | |
| RU | 2641970 C2 | 1/2018 | | |
| RU | 2696007 C1 | 7/2019 | | |
| WO | WO 2004067031 A1 | 8/2004 | | |
| WO | 2008084294 A2 | 7/2008 | | |
| WO | WO 2013181086 A1 | 12/2013 | | |
| WO | WO 2014029702 A1 | 2/2014 | | |
| WO | 2014147001 A1 | 9/2014 | | |
| WO | WO-2020142778 A1 * | 7/2020 | ........... | A61K 39/099 |

OTHER PUBLICATIONS

Hess et al. 2011 (Evaluation of efficacy of oral administration of Bordetella bronchiseptica intranasal vaccine when used to protect puppies from the tracheobronchitis due to B. bronchiseptica infection) (Year: 2011).*

Hess et al. 2011 (Evaluation of Efficacy of Oral Administration of Bordetella bronchiseptica Intranasal vaccine when used to protect puppies from tracheobronchitis due to B. bronchiseptica infection; Intern J Appl Res Vet Med; 9(3): 300-305). (Year: 2011).*

Kontor et al., 1981, "Canine infectious tracheobronchitis: effects of an intranasal live canine parainfluenza—Bordetella bronchiseptica vaccine on viral shedding and clinical tracheobronchitis (kennel cough)," Am. J. Vet. Res., 42(10):1694-1698.

Shubin, 2017, "canine infectious tracheobronchitis (kennel cough)," Veterinary clinic of Dr. Balakovo Shubin, Dec. 13, 2017. Retrieved from the Internet (Wayback Machine):< URL: https://web.archive.org/web/20171213201727/https://balakovo-vet.ru/content/infekcionnyy-traheobronhit-sobak-kompleks-volernogo-kashlya> in Russian with machine English translation (4 pages).

Chen, Zhenhai et al., A Novel Rabies Vaccine Based on a Recombinant Parainfluenza Virus 5 Expressing Rabies Virus Glycoprotein, Journal of Virology, 2013, 2986-2993, 87:6.

Chen, Zhenhai, Parainfluenza virus 5—vectored vaccines against human and animal infectious diseases, Rev Med Virol., 2018, 1-8, 28:e1965.

(Continued)

*Primary Examiner* — Mary Maille Lyons

(74) *Attorney, Agent, or Firm* — Susanna C. Benn

(57) ABSTRACT

The present invention is drawn to new oral live canine parainfluenza virus vaccines and related multivalent vaccines. Methods of using the vaccine alone or in combination with one or more other protective immunogens in multivalent vaccines are also provided.

10 Claims, No Drawings

(56)                    References Cited

OTHER PUBLICATIONS

Hess, Thomas J. et al., Evaluation of Efficacy of Oral Administration of Bordetella bronchiseptica Intranasal Vaccine When Used to Protect Puppies from Tracheobronchitis Due to B bronchiseptica Infection, The Journal of Applied Research in Veterinary Medicine, 2011, 300-305, 9(3).

Jacobs, A. A. C. et al., Compatibility of a bivalent modified-live vaccine against Bordetella bronchiseptica and CPiV, and a trivalent modified-live vaccine against CPV, CDV and CAV-2, Veterinary Record, 2007, 41-45, 160.

Jacobs, A. A. C. et al., Protection of dogs for 13 months against Bordetella bronchiseptica and canine parainfluenza virus with a modified live vaccine, Veterinary Record, 2005, 19-23, 157.

Lehr, Craig et al., Demonstration of 1-Year Duration of Immunity for Attenuated Bordetella bronchiseptica Vaccines in Dogs, Veterinary Therapeutics, 2008, 257-262, 9:4.

Merck Animal Health product label for Nobivac Canine 1-DAPPv, downloaded Jun. 1, 2022.

Merck Animal Health product label for Nobivac Intra-Trac 3, downloaded Jun. 1, 2022.

Merck Animal Health product label for Nobivac Intra-Trac KC downloaded Jun. 1, 2022.

United States Department of Agriculture, Center for Veterinary Biologics, Testing Protocol, "SAM 113—Supplemental Assay Method for Titration of Parainfluenza 3 Neutralizing Antibody (Constant Virus—Varying Serum Method)," No. 113.05, May 12, 2017 (17 pages).

United States Department of Agriculture, Center for Veterinary Biologics, Testing Protocol, "SAM 309—Supplemental Assay Method for Titration of Canine Parainfluenza Virus in Vero Cell Culture," No. 309.05, Oct. 30, 2014 (13 pages).

United States Patent and Trademark Office, Certified U.S. Appl. No. 62/788,764, filed Jan. 4, 2019 by Merial Inc. (79 pages).

United States Department of Agriculture Center for Veterinary Biologics Testing Protocol SAM 309: Supplemental Assay Method for Titration of Canine Parainfluenza Virus in Vero Cell Culture; Oct. 30, 2014, signed Jan. 9 & 13, 2015; Srinivas, Geetha B; 13 Pages.†

U.S. Appl. No. 62/788,764; filed Jan. 4, 2019; First Named Inventor: Laurent Bernard; 79 Pages.†

United States Department of Agriculture Center for Veterinary Biologics Testing Protocol SAM 113: Supplemental Assay Method for Titration of Parainfluenza 3 Neutralizing Antibody (Constant Virus—Varying Serum Method); Dated May 12, 2017, signed Jul. 12 & 13, 2017; Srinivas, Geetha B.; 17 Pages.†

\* cited by examiner

† cited by third party

ORAL RESPIRATORY VACCINE

CROSS-REFERENCE TO RELATED APPLICATIONS

This application is a National Stage application of International Patent Application No. PCT/EP2020/086683 filed Dec. 17, 2020 which claims priority to U.S. Provisional Patent Application No. 62/949,928, filed Dec. 18, 2019.

FIELD OF THE INVENTION

The present invention relates to new oral live canine parainfluenza virus vaccines and related multivalent vaccines. Methods of making and using the vaccine alone or in combination with one or more other protective antigens in multivalent vaccines are also provided.

BACKGROUND OF THE INVENTION

Canine parainfluenza (CPI) virus is a highly contagious virus that causes respiratory illnesses contributing to the contraction of upper respiratory diseases and infectious tracheobronchitis, also known as kennel cough. Although the respiratory signs may resemble those of canine influenza, they are unrelated viruses and require different vaccines for protection. CPI virus is excreted from the respiratory tract of infected animals for up to two weeks after infection and is usually transmitted through the air. CPI virus spreads rapidly in kennels or shelters, where large numbers of dogs are kept together. Clinical signs include either dry or moist coughing, low grade fever, nasal discharge, lack of energy, and loss of appetite.

Currently, there are several commercial canine vaccines that can be administered either subcutaneously or intramuscularly that comprise a live modified CPI virus including Nobivac® Canine 1-DAPPv, which is a modified live virus vaccine for the vaccination of healthy dogs as an aid in the prevention of disease caused by canine parainfluenza virus, canine distemper virus, canine adenovirus, and canine parvovirus. In addition, there are commercial intranasal vaccines, such as Nobivac® Intra-Trac₃, that provides triple protection against agents implicated in the cause of tracheobronchitis, including canine parainfluenza virus, canine adenovirus type 2, and *Bordetella bronchiseptica* (*B. bronchiseptica*).

However, despite the advantages of oral vaccination, such as ease of use and lack of animal discomfort during and following vaccination, to date there have been no commercially available oral vaccines containing CPI virus. Therefore, there remains the longstanding need for oral vaccines for canine parainfluenza virus that will aid in the protection of dogs from upper respiratory diseases and/or infectious tracheobronchitis.

The citation of any reference herein should not be construed as an admission that such reference is available as "prior art" to the instant application.

SUMMARY OF THE INVENTION

The present invention provides vaccine compositions for oral administration to animal subjects, such as canines, that include an immunologically effective amount of a modified live canine parainfluenza (CPI) virus that aids in eliciting protective immunity in (and/or provides effective protection to) the recipient vaccinated animal subject. In certain embodiments, the titer of the modified live CPI virus in the vaccine is equal to or greater than $6.0 \log_{10}HAID_{50}/mL$. In other embodiments, the titer of the modified live CPI virus in the vaccine is equal to or greater than $6.3 \log_{10}HAID_{50}/mL$. In still other embodiments, the titer of the modified live CPI virus in the vaccine is equal to or greater than $6.5 \log_{10}HAID_{50}/mL$. In yet other embodiments, the titer of the modified live CPI virus in the vaccine is equal to or greater than $6.7 \log_{10}HAID_{50}/mL$. In still other embodiments, the titer of the modified live CPI virus in the vaccine is equal to or greater than $6.9 \log_{10}HAID_{50}/mL$. In yet other embodiments, the titer of the modified live CPI virus in the vaccine is equal to or greater than $7.1 \log_{10}HAID_{50}/mL$. In still other embodiments, the titer of the modified live CPI virus in the vaccine is equal to or greater than $7.3 \log_{10}HAID_{50}/mL$. In yet other embodiments, the titer of the modified live CPI virus in the vaccine is equal to or greater than $7.6 \log_{10}HAID_{50}/mL$. In still other embodiments, the titer of the modified live CPI virus in the vaccine is equal to or greater than $7.8 \log_{10}HAID_{50}/mL$. In yet other embodiments, the titer of the modified live CPI virus in the vaccine is equal to or greater than $8.0 \log_{10}HAID_{50}/mL$. In still other embodiments, the titer of the modified live CPI virus in the vaccine is equal to or greater than $8.3 \log_{10}HAID_{50}/mL$. In yet other embodiments, the titer of the modified live CPI virus in the vaccine is equal to or greater than $8.6 \log_{10}HAID_{50}/mL$. In still other embodiments, the titer of the modified live CPI virus in the vaccine is equal to or greater than $8.8 \log_{10}HAID_{50}/mL$.

In related embodiments of the oral vaccine, the titer of the modified live CPI virus in the vaccine is $6.0 \log_{10}HAID_{50}/mL$ to $9.5 \log_{10}HAID_{50}/mL$. In other embodiments of the oral vaccine, the titer of the modified live CPI virus in the vaccine is $6.5 \log_{10}HAID_{50}/mL$ to $9.5 \log_{10}HAID_{50}/mL$. In yet other embodiments, the titer of the modified live CPI virus in the vaccine is $6.8 \log_{10}HAID_{50}/mL$ to $9.5 \log_{10}HAID_{50}/mL$. In still other embodiments, the titer of the modified live CPI virus in the vaccine is $7.0 \log_{10}HAID_{50}/mL$ to $9.5 \log_{10}HAID_{50}/mL$. In yet other embodiments, the titer of the modified live CPI virus in the vaccine is $7.3 \log_{10}HAID_{50}/mL$ to $9.5 \log_{10}HAID_{50}/mL$. In still other embodiments, the titer of the modified live CPI virus in the vaccine is $7.3 \log_{10}HAID_{50}/mL$ to $8.6 \log_{10}HAID_{50}/mL$.

In specific embodiments of the vaccines comprising a modified live CPI virus, the CPI virus shares the unique/identifying characteristics of the modified live CPI virus having the ATCC accession No. PTA-126273. In more particular embodiments, the modified live CPI virus in the vaccines has the ATCC accession No. PTA-126273.

The present invention further provides vaccines for oral administration to animal subjects, that aid in eliciting (and/or elicit) protective immunity (and/or provides effective protection) in the recipient vaccinated animal subject that include a modified live canine parainfluenza (CPI) virus and further comprise an avirulent live *B. bronchiseptica*. In particular embodiments, in addition to comprising one of the aforesaid quantities of the modified live CPI virus, the vaccine further comprises a titer of the avirulent live *B. bronchiseptica* equal to $1 \times 10^7$ cfu/mL to $1 \times 10^{12}$ cfu/mL. In other embodiments, the vaccine comprises a titer of the avirulent live *B. bronchiseptica* equal to $1 \times 10^8$ cfu/mL to $1 \times 10^{12}$ cfu/mL. In still other embodiments, the vaccine comprises a titer of the avirulent live *B. bronchiseptica* equal to $5 \times 10^8$ cfu/mL to $1 \times 10^{12}$ cfu/mL. In yet other embodiments, the vaccine comprises a titer of the avirulent live *B. bronchiseptica* of $1 \times 10^9$ cfu/mL to $5 \times 10^{11}$ cfu/mL.

The oral vaccines of the present invention can comprise a modified live canine parainfluenza virus, with or without an avirulent live *B. bronchiseptica*, but with one or more additional immunogens. In certain embodiments, the vaccine further comprises a live attenuated canine influenza virus. In other embodiments, the vaccine further comprises a live attenuated canine parvovirus. In still other embodiments, the vaccine further comprises a live attenuated canine distemper virus. In yet other embodiments, the vaccine further comprises a live attenuated canine adenovirus type 2. In still other embodiments, the vaccine further comprises a live attenuated respiratory canine coronavirus. In yet other embodiments, the vaccine further comprises a live attenuated canine pneumovirus. In still other embodiments, the vaccine further comprises a viral vector encoding one or more protein immunogens from a canine influenza virus, canine parvovirus, canine distemper virus, canine adenovirus (Type 1 or 2), a respiratory canine coronavirus, canine pneumovirus, *Streptococcus equi zooepidemicus* and/or *Mycoplasma cynos*. In yet other embodiments, the vaccine further comprises a live attenuated *Streptococcus equi zooepidemicus*. In still other embodiments, the vaccine further comprises a live attenuated *Mycoplasma cynos*. In addition, vaccines that comprise either a modified live canine parainfluenza virus or a modified live canine parainfluenza virus with an avirulent live *B. bronchiseptica* can further comprise two or more of these other immunogens. The vaccines of the present invention may be adjuvanted or non-adjuvanted.

The present invention further provides methods of aiding in the protection of (and/or providing effective protection to) a canine from upper respiratory diseases and infectious tracheobronchitis comprising orally administering to the canine a vaccine comprising a modified live canine parainfluenza virus. In certain embodiments of this method, the titer of the modified live CPI virus administered is equal to or greater than $6.0 \log_{10}\text{HAID}_{50}$/dose. In other embodiments of this method, the titer of the modified live CPI virus administered is equal to or greater than $6.3 \log_{10}\text{HAID}_{50}$/dose. In yet other embodiments of this method, the titer of the modified live CPI virus administered is equal to or greater than $6.5 \log_{10}\text{HAID}_{50}$/dose. In still other embodiments of this method, the titer of the modified live CPI virus administered is equal to or greater than $6.7 \log_{10}\text{HAID}_{50}$/dose. In yet other embodiments of this method, the titer of the modified live CPI administered is equal to or greater than $7.0 \log_{10}\text{HAID}_{50}$/dose. In still other embodiments of this method, the titer of the modified live CPI virus administered is equal to or greater than $7.3 \log_{10}\text{HAID}_{50}$/dose. In yet other embodiments of this method, the titer of the modified live CPI administered is equal to or greater than $7.6 \log_{10}\text{HAID}_{50}$/dose. In still other embodiments of this method, the titer of the modified live CPI virus administered is equal to or greater than $7.8 \log_{10}\text{HAID}_{50}$/dose. In yet other embodiments of this method, the titer of the modified live CPI administered is equal to or greater than $8.0 \log_{10}\text{HAID}_{50}$/dose. In still other embodiments of this method, the titer of the modified live CPI virus administered is equal to or greater than $8.3 \log_{10}\text{HAID}_{50}$/dose. In yet other embodiments of this method, the titer of the modified live CPI administered is equal to or greater than $8.6 \log_{10}\text{HAID}_{50}$/dose. In still other embodiments of this method, the titer of the modified live CPI virus administered is equal to or greater than $8.8 \log_{10}\text{HAID}_{50}$/dose.

In related embodiments of this method, the titer of the modified live CPI virus administered is $6.0 \log_{10}\text{HAID}_{50}$/dose to $9.5 \log_{10}\text{HAID}_{50}$/dose. In other embodiments of this method, the titer of the modified live CPI virus administered is $6.3 \log_{10}\text{HAID}_{50}$/dose to $9.5 \log_{10}\text{HAID}_{50}$/dose. In yet other embodiments of this method, the titer of the modified live CPI virus administered is $6.5 \log_{10}\text{HAID}_{50}$/dose to $9.5 \log_{10}\text{HAID}_{50}$/dose. In still other embodiments of this method, the titer of the modified live CPI virus administered is $6.8 \log_{10}\text{HAID}_{50}$/dose to $9.5 \log_{10}\text{HAID}_{50}$/dose. In yet other embodiments of this method, the titer of the modified live CPI virus administered is $7.0 \log_{10}\text{HAID}_{50}$/dose to $9.5 \log_{10}\text{HAID}_{50}$/dose. In still other embodiments of this method the titer of the modified live CPI virus administered is $7.3 \log_{10}\text{HAID}_{50}$/dose to $9.5 \log_{10}\text{HAID}_{50}$/dose. In yet other embodiments of this method, the titer of the modified live CPI virus administered is $7.3 \log_{10}\text{HAID}_{50}$/dose to $9.0 \log_{10}\text{HAID}_{50}$/dose. In specific embodiments of the methods of orally administering a vaccine comprising a modified live CPI virus, the CPI virus shares the unique/identifying characteristics of the modified live CPI virus having the ATCC accession No. PTA-126273. In more particular embodiments of the methods of the present invention, the modified live CPI virus has the ATCC accession No. PTA-126273.

In one aspect of the present invention, the method of aiding in the protection of (and/or providing effective protection to) a canine from upper respiratory diseases and infectious tracheobronchitis comprises orally administering to the animal subject, e.g., a canine, a vaccine comprising a modified live CPI virus that further comprises an avirulent live *B. bronchiseptica* (i.e., a vaccine comprising both a modified live CPI virus and an avirulent live *B. bronchiseptica*). In certain embodiments of this method, in addition to comprising one of the aforesaid quantities of the modified live CPI virus, the vaccine also comprises a titer of the avirulent live *B. bronchiseptica* equal to or greater than $1\times10^7$ cfu/dose. In particular embodiments of this method, the titer of the avirulent live *B. bronchiseptica* is equal to or greater than $5\times10^7$ cfu/dose. In more particular embodiments of this method, the titer of the avirulent live *B. bronchiseptica* is equal to or greater than $1\times10^8$ cfu/dose. In even more particular embodiments of this method, the titer of the avirulent live *B. bronchiseptica* is equal to or greater than $5\times10^8$ cfu/dose. In specific embodiments, the titer of the avirulent live *B. bronchiseptica* is equal to or greater than $1\times10^9$ cfu/dose. In related embodiments of the method, the titer of the avirulent live *B. bronchiseptica* is $1\times10^7$ cfu/dose to $1\times10^{12}$ cfu/dose. In yet other embodiments of the method, the titer of the avirulent live *B. bronchiseptica* is $1\times10^9$ cfu/dose to $1\times10^{12}$ cfu/dose. In still other embodiments of the method, the titer of the avirulent live *B. bronchiseptica* is $1\times10^8$ cfu/dose to $5\times10^{11}$ cu/dose. In yet other embodiments of the method, the titer of the avirulent live *B. bronchiseptica* is $5\times10^8$ cfu/dose to $5\times10^{11}$ cfu/dose. In still other embodiments of the method, the titer of the avirulent live *B. bronchiseptica* is $1\times10^9$ cfu/dose to $5\times10^{11}$ cfu/dose. In yet other embodiments of the method, the titer of the avirulent live *B. bronchiseptica* is $5\times10^9$ cfu/dose to $5\times10^{11}$ cfu/dose.

In more particular embodiments of the method, the titer of the modified live CPI virus is equal to or greater than $6.0 \log_{10}\text{HAID}_{50}$/dose and the titer of the avirulent live *B. bronchiseptica* is equal to or greater than $1\times10^7$ cfu/dose. In still more particular embodiments of the method, the titer of the modified live CPI virus is equal to or greater than $6.5 \log_{10}\text{HAID}_{50}$/dose and the titer of the avirulent live *B. bronchiseptica* is equal to or greater than $1\times10^7$ cfu/dose. In yet more particular embodiments of the method, the titer of the modified live CPI virus is equal to or greater than $6.5 \log_{10}\text{HAID}_{50}$/dose and the titer of the avirulent live *B. bonchiseptica* is equal to or greater than $5\times10^8$ cfu/dose.

In certain embodiments of the method, the titer of the modified live CPI virus is equal to or greater than 6.0 $\log_{10}HAID_{50}$/dose to 9.5 $\log_{10}HAID_{50}$/dose and the titer of the avirulent live *B. bronchiseptica* is equal to or greater than $1\times10^7$ cfu/dose. In other embodiments of the method, the titer of the modified live CPI virus is equal to or greater than 6.5 $\log_{10}HAID_{50}$/dose to 9.5 $\log_{10}HAID_{50}$/dose and the titer of the avirulent live *B. bronchiseptica* is equal to or greater than $1\times10^7$ cfu/dose. In still other embodiments of this method, the titer of the modified live CPI virus is 6.8 $\log_{10}HAID_{50}$/dose to 9.5 $\log_{10}HAID_{50}$/dose and the titer of the avirulent live *B. bronchiseptica* is equal to or greater than $1\times10^7$ cfu/dose. In yet other embodiments of this method, the titer of the modified live CPI virus is 6.8 $\log_{10}HAID_{50}$/dose to 9.5 $\log_{10}HAID_{50}$/dose and the titer of the avirulent live *B. bronchiseptica* is equal to or greater than $1\times10^9$ cfu/dose. In still other embodiments, the titer of the modified live CPI virus is 7.0 $\log_{10}HAID_{50}$/dose to 9.0 $\log_{10}HAID_{50}$/dose and the titer of the avirulent live *B. bronchiseptica* is equal to or greater than $1\times10^7$ cfu/dose. In yet other embodiments, the titer of the modified live CPI virus is 7.0 $\log_{10}HAID_{50}$/dose to 9.0 $\log_{10}HAID_{50}$/dose and the titer of the avirulent live *B. bronchiseptica* is equal to or greater than $1\times10^9$ cfu/dose.

In still other embodiments of the method, the titer of the modified live CPI virus is equal to or greater than 6.0 $\log_{10}HAID_{50}$/dose and the titer of the avirulent live *B. bronchiseptica* is $5\times10^8$ cfu/dose to $5\times10^{11}$ cfu/dose. In yet other embodiments of the method, the titer of the modified live CPI virus is equal to or greater than 6.5 $\log_{10}HAID_{50}$/dose and the titer of the avirulent live *B. bronchiseptica* is $5\times10^8$ cfu/dose to $5\times10^{11}$ cfu/dose. In still other embodiments of the method, the titer of the modified live CPI virus is equal to or greater than 6.5 $\log_{10}HAID_{50}$/dose and the titer of the avirulent live *B. bronchiseptica* is $5\times10^9$ cfu/dose to $5\times10^{11}$ cfu/dose.

In other embodiments of this method, the titer of the modified live CPI virus is 6.0 $\log_{10}HAID_{50}$/dose to 9.5 $\log_{10}HAID_{50}$/dose and the titer of the avirulent live *B. bronchiseptica* is $5\times10^8$ cfu/dose to $5\times10^{11}$ cfu/dose. In yet other embodiments of this method, the titer of the modified live CPI virus is 6.5 $\log_{10}HAID_{50}$/dose to 9.5 $\log_{10}HAID_{50}$/dose and the titer of the avirulent live *B. bronchiseptica* is $5\times10^8$ cfu/dose to $5\times10^{11}$ cfu/dose. In still other embodiments, the titer of the modified live CPI virus is 6.5 $\log_{10}HAID_{50}$/dose to 9.5 $\log_{10}HAID_{50}$/dose and the titer of the avirulent live *B. bronchiseptica* is $5\times10^9$ cfu/dose to $5\times10^{11}$ cfu/dose. In yet other embodiments of this method, the titer of the modified live CPI virus is 6.8 $\log_{10}HAID_{50}$/dose to 9.0 $\log_{10}HAID_{50}$/dose and the titer of the avirulent live *B. bronchiseptica* is $5\times10^8$ cfu/dose to $5\times10^{11}$ cfu/dose. In still other embodiments of this method, the titer of the modified live CPI virus is 6.8 $\log_{10}HAID_{50}$/dose to 9.5 $\log_{10}HAID_{50}$/dose and the titer of the avirulent live *B. bronchiseptica* is $5\times10^9$ cfu/dose to $5\times10^{11}$ cfu/dose. In yet other embodiments, the titer of the modified live CPI virus is 7.0 $\log_{10}HAID_{50}$/dose to 9.0 $\log_{10}HAID_{50}$/dose and the titer of the avirulent live *B. bronchiseptica* is $5\times10^8$ cfu/dose to $5\times10^{11}$ cfu/dose. In still other embodiments, the titer of the modified live CPI virus is 7.0 $\log_{10}HAID_{50}$/dose to 9.0 $\log_{10}HAID_{50}$/dose and the titer of the avirulent live *B. bronchiseptica* is $5\times10^9$ cfu/dose to $5\times10^{11}$ cfu/dose.

In specific embodiments of the methods of orally administering a vaccine comprising a modified live CPI virus and an avirulent live *B. bronchiseptica*, the avirulent live *B. bronchiseptica* virus shares the unique/identifying characteristics of the avirulent live *B. bronchiseptica* having the ATCC accession No. PTA-126272. In more specific embodiments of the method, the avirulent live *B. bronchiseptica* has the ATCC accession No. PTA-126272. In still more specific embodiments, the modified live CPI virus has the ATCC accession No. PTA-126273 and the avirulent live *B. bronchiseptica* has the ATCC accession No. PTA-126272.

In other embodiments, the methods of aiding in the protection of (and/or providing effective protection to) a canine from upper respiratory diseases and infectious tracheobronchitis comprises orally administering a vaccine that comprises a modified live canine parainfluenza virus and one or more additional immunogens. In certain embodiments of the methods, the vaccine further comprises a live attenuated canine influenza virus. In other embodiments of the methods, the vaccine further comprises a live attenuated canine parvovirus. In still other embodiments of the methods, the vaccine further comprises a live attenuated canine distemper virus. In yet other embodiments of the methods, the vaccine further comprises a live attenuated canine adenovirus type 2. In still other embodiments of the methods, the vaccine further comprises a live attenuated respiratory canine coronavirus. In yet other embodiments of the methods, the vaccine further comprises a live attenuated canine pneumovirus. In still other embodiments of the methods, the vaccine further comprises one or more viral vectors encoding one or more protein immunogens from a canine influenza virus, canine parvovirus, canine distemper virus, canine adenovirus (Type 1 or 2), respiratory canine coronavirus, canine pneumovirus, *Streptococcus equi zooepidemicus* and/or *Mycoplasma cynos*. In still other embodiments of the methods, the vaccine further comprises a live attenuated *Streptococcus equi zooepidemicus*. In yet other embodiments of the methods, the vaccine further comprises a live attenuated *Mycoplasma cynos*. In addition, the methods of aiding in the protection of (and/or providing effective protection to) a canine from upper respiratory diseases and infectious tracheobronchitis can comprise orally administering a vaccine that comprises a modified live canine parainfluenza virus in combination with two or more of these immunogens.

In related embodiments, the method of aiding in the protection of (and/or providing effective protection to) a canine from upper respiratory diseases and infectious tracheobronchitis comprises orally administering to the canine a vaccine comprising a modified live canine parainfluenza virus, an avirulent live *B. bronchiseptica*, and one or more additional live attenuated immunogens. In certain embodiments of the methods, the vaccine further comprises a live attenuated canine influenza virus. In other embodiments of the methods, the vaccine further comprises a live attenuated canine parvovirus. In still other embodiments of the methods, the vaccine further comprises a live attenuated canine distemper virus. In yet other embodiments of the methods, the vaccine further comprises a live attenuated canine adenovirus type 2. In still other embodiments of the methods, the vaccine further comprises a live attenuated respiratory canine coronavirus. In yet other embodiments of the methods, the vaccine further comprises a live attenuated canine pneumovirus. In still other embodiments of the methods, the oral vaccine further comprises a viral vector encoding one or more protein immunogens from a canine influenza virus, canine parvovirus, canine distemper virus, canine adenovirus (Type 1 or 2), respiratory canine coronavirus, canine pneumovirus, *Streptococcus equi zooepidemicus* and/or *Mycoplasma cynos*. In still other embodiments of the methods, the vaccine further comprises a live attenuated *Streptococcus equi zooepidemicus*. In yet other embodiments of the methods, the vaccine further comprises a live attenuated *Mycoplasma cynos*. In addition, the methods of aiding in the protection of (and/or providing effective protection to) a canine from upper respiratory diseases and infectious tracheobronchitis can comprise orally administering a vaccine that comprises a modified live canine parainfluenza virus and an avirulent *B. bronchiseptica* in combination with two or more of these immunogens.

In specific embodiments, the method of aiding in the protection of (and/or providing effective protection to) a canine from upper respiratory diseases and infectious tracheobronchitis comprises orally administering a vaccine comprising a modified live canine parainfluenza virus, a live attenuated canine parvovirus, a live attenuated canine distemper virus, a live attenuated canine adenovirus type 2, and an avirulent live *B. bronchiseptica*.

In certain embodiments, a method of aiding in the protection of (and/or providing effective protection to) a canine from upper respiratory diseases and infectious tracheobronchitis of the present invention can comprise orally administering to the canine a single-dose vaccine. Accordingly, in specific embodiments, the method comprises orally administering to the canine a single-dose vaccine comprising a modified live canine parainfluenza virus. In related embodiments, the method comprises orally administering to the canine a single-dose vaccine comprising both a modified live canine parainfluenza virus and an avirulent live *B. bronchiseptica*.

In alternative embodiments, a method of aiding in the protection of (and/or providing effective protection to) a canine from upper respiratory diseases and infectious tracheobronchitis of the present invention can comprise orally administering to the canine two or more doses of the vaccine. Accordingly, in specific embodiments, the method comprises orally administering to the canine two or more doses of a vaccine comprising a modified live canine parainfluenza virus. In related embodiments, the method comprises orally administering to the canine two or more doses of a vaccine comprising both a modified live canine parainfluenza virus and an avirulent live *B. bronchiseptica*.

In particular embodiments, the method of aiding in the protection of (and/or providing effective protection to) a canine from upper respiratory diseases and infectious tracheobronchitis comprises orally administering to the canine a non-adjuvanted vaccine. Specific embodiments of these methods comprise orally administering to the canine a vaccine comprising a modified live canine parainfluenza virus, in which the vaccine is a non-adjuvanted vaccine. More particular embodiments of these methods comprise orally administering to the canine a vaccine comprising a modified live canine parainfluenza virus and an avirulent live *B. bronchiseptica* in which the vaccine is a non-adjuvanted vaccine. In particular embodiments of this type, the vaccines are administered as a single-dose vaccine.

Alternative embodiments of methods of aiding in the protection of (and/or providing effective protection to) a canine from upper respiratory diseases and infectious tracheobronchitis comprise orally administering to the canine an adjuvanted vaccine. Particular embodiments of these methods comprise orally administering to the canine a vaccine comprising a modified live canine parainfluenza virus, in which the vaccine comprises an adjuvant. Related embodiments of these methods comprise orally administering to the canine a vaccine comprising both a modified live canine parainfluenza virus and an avirulent live *B. bronchiseptica*, in which the vaccine comprises an adjuvant. In particular embodiments of this type, the vaccines are administered as a single-dose vaccine.

In certain embodiments of the methods of aiding in the protection of (and/or providing effective protection to) a canine from upper respiratory diseases and infectious tracheobronchitis, a vaccine of the present invention is orally administered in a dose of 0.2 mL to 5 mL. In related embodiments, a vaccine of the present invention is orally administered in a dose of 0.2 mL to 4 mL. In other particular embodiments, a vaccine of the present invention is orally administered in a dose of 0.3 to 1.5 mL. In still other embodiments, a vaccine of the present invention is orally administered in a dose of 0.2 mL to 3.0 mL. In yet other embodiments, a vaccine of the present invention is orally administered in a dose of 0.2 mL to 2.5 mL. In still other embodiments, a vaccine of the present invention is orally administered in a dose of 0.2 mL to 2.0 mL. In yet other embodiments, a vaccine of the present invention is orally administered in a dose of 0.5 to 2.5 mL. In still other embodiments, a vaccine of the present invention is orally administered in a dose of 0.75 mL to 2.0 mL. In yet other embodiments, a vaccine of the present invention is orally administered in a dose of 0.5 mL to 2.0 mL. In still other embodiments, a vaccine of the present invention is orally administered in a dose of 0.5 mL to 1.5 mL. In yet other embodiments, a vaccine of the present invention is orally administered in a dose of 0.75 mL to 1.5 mL. In specific embodiments, the vaccines of the present invention are orally administered in a dose of 1.0 mL.

These and other aspects of the present invention will be better appreciated by reference to the following Detailed Description, including the Examples below.

DETAILED DESCRIPTION OF THE INVENTION

Accordingly, the present invention provides modified live canine parainfluenza virus vaccines, including multivalent vaccines useful as oral vaccines. The present invention also provides methods of orally immunizing a canine against canine parainfluenza virus, comprising oral administration to a canine of a vaccine comprising a modified live canine parainfluenza (CPI) virus. The present invention further provides single-dose vaccines that comprise a modified live canine parainfluenza virus. Such vaccines aid in the protection of (and/or provide effective protection to) the vaccinated canine for at least 6 months against upper respiratory diseases and infectious tracheobronchitis, without the need of a booster vaccine. In certain embodiments, the single-dose vaccine is administered in a 1 mL dose to the canine.

The present invention further provides vaccines comprising a modified live canine parainfluenza virus in combination with one or more other canine pathogens and/or immunogens that further elicit immunity to canine influenza virus (e.g., H3N2 and/or H3N8), canine parvovirus, canine distemper virus, canine adenovirus, canine respiratory coronavirus, canine pneumovirus, *Mycoplasma* species (e.g., *Mycoplasma cynos*), and *Streptococcus equi zooepidemicus*.

More specifically, the present invention also includes multivalent oral vaccines comprising modified live canine parainfluenza virus together with an avirulent live *B. bronchiseptica*. The present invention further provides methods of immunizing a canine against canine parainfluenza virus and *B. bronchiseptica*, comprising oral administration to a canine of a vaccine comprising a modified live canine parainfluenza virus and an avirulent live *B. bronchiseptica*. In specific embodiments of the present invention, a canine receiving only one dose of a single-dose vaccine (or multivalent vaccine) comprising a modified live canine parainfluenza virus and an avirulent live *B. bronchiseptica* is protected for at least 6 months against upper respiratory diseases and infectious tracheobronchitis caused by a wild type CPI virus and a wild type avirulent live *B. bronchiseptica*, without the need of a booster vaccine. In more specific embodiments, the single-dose vaccine is administered in a 1 mL dose to the canine.

In particular embodiments, the vaccines comprise an immunologically effective amount of a modified live CPI virus and the avirulent live *B. bronchiseptica*, as determined by the amount of CPI virus serum neutralizing antibodies and *B. bronchiseptica* agglutinating and/or IgA antibodies induced in a vaccinated canine. In a related aspect, the present invention provides a vaccine that comprises a specific, minimum amount of each antigen that is effective against virulent CPI virus and virulent *B. bronchiseptica*. In yet another aspect, a vaccine of the present invention is both safe and effective and aids in the protection of (and/or provides effective protection to) a canine from upper respiratory diseases and infectious tracheobronchitis due to CPI virus and *B. bronchiseptica* infections in dogs.

The present invention also provides multivalent vaccines comprising a live attenuated CPI virus and an avirulent live *B. bronchiseptica* in further combination with one or more other canine pathogens and/or immunogens that further elicit immunity to canine influenza virus (e.g., H3N2 and H3N8), canine parvovirus, canine adenovirus, canine distemper virus, canine adenovirus, canine respiratory coronavirus, canine pneumovirus, *Mycoplasma* species (e.g., *Mycoplasma cynos*) and *Streptococcus equi zooepidemicus*.

As used herein the term "approximately" is used interchangeably with the term "about" and signifies that a value is within twenty-five percent of the indicated value i.e., a dose of a vaccine comprising "approximately" 4.0 mL can contain 3.0 to 5.0 mL.

As used herein the term, "canine" is used interchangeably with the term "dog" and includes all domestic dogs, i.e., *Canis lupus familiaris* or *Canis familiaris*, unless otherwise indicated.

As used herein, the term "feline" refers to any member of the Felidae family. Domestic cats, pure-bred and/or mongrel companion cats, and wild or feral cats are all felines.

As used herein, a "vaccine" is a composition that is suitable for application to an animal, e.g., a canine, and comprises one or more antigens, i.e., one or more immunogens, typically combined with a pharmaceutically acceptable carrier such as a liquid containing sterile water, which upon administration to the animal induces an immune response strong enough to minimally aid in the protection (and/or provide effective protection) from a disease arising from an infection with a wild-type micro-organism (e.g., virus or bacterium), i.e., strong enough for aiding in the prevention of the disease, providing effective protection, preventing, or ameliorating the disease. In preferred embodiments, the vaccine is strong enough to provide effective protection from a disease arising from an infection with a wild-type micro-organism (e.g., virus or bacterium). The use here, of the term "vaccine" encompasses both monovalent vaccines and multivalent vaccines. A vaccine for oral administration to an animal subject also can be termed an "oral vaccine".

As used herein, a "multivalent vaccine" is a vaccine that comprises two or more different antigens. In particular embodiments of this type, the multivalent vaccine stimulates the immune system of the recipient against two or more different pathogens.

As used herein, the terms "protect", "protecting", "provides effective protection" "providing effective protection", "aids in the protection", "aiding in the protection" and "aids in eliciting protective immunity" do not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

As used herein, the terms "providing effective protection" and "provides effective protection" are used interchangeably. "Providing effective protection" to a canine from upper respiratory diseases and infectious tracheobronchitis, with respect to a modified live canine parainfluenza virus comprised by a vaccine of the present invention is determined by finding a statistically significant decrease in the duration of CPI virus shedding and/or clinical signs of disease between vaccinated dogs and placebo-vaccinated control dogs following a challenge with live wild type CPI virus. "Providing effective protection" to a canine from upper respiratory diseases and infectious tracheobronchitis, with respect to an avirulent live *B. bronchiseptica* comprised by a vaccine of the present invention is determined by finding a statistically significant decrease in the number of affected dogs between vaccinated dogs and placebo-vaccinated control dogs following a challenge with live wild type *B. bronchiseptica*. An affected dog is defined as having spontaneous coughing or spontaneous coughing with retching on two or more consecutive days during the post-challenge observation period.

As used herein, the "duration of viral shedding" is the number of days from the first to last occurrence that the virus was shed from the nare of a canine as determined by virus titration from nasal swabs. In particular embodiments of the present invention, the duration of viral shedding is determined for the CPI virus.

As used herein, the "duration of bacterial shedding" is the number of days from the first to last occurrence that the bacteria were shed from the nare of a canine as determined by bacterial titration from nasal swabs. In particular embodiments of the present invention, the duration of bacterial shedding is determined for *B. bronchiseptica*.

As used herein, a canine that "seroconverts" means that the canine's antibody titer to a specific antigen (e.g., a CPI virus or a *B. bronchiseptica*) is at least 2-fold greater than the baseline value for that specific antigen.

As used herein, the terms "live attenuated virus" and "live modified virus" are used interchangeably and are live attenuated viral immunogens that are immunogenic, but not pathogenic.

As used herein, the terms "live attenuated bacterium", "avirulent live culture of a bacterium", and "avirulent live bacterium" are used interchangeably and are live attenuated bacterial immunogens (e.g., an avirulent live *B. bonchiseptica*) that are immunogenic, but not pathogenic.

As used herein, when a "dose" of a vaccine to be administered to an animal subject is defined as comprising a specific quantity or range of quantities of antigen e.g., by weight such as 4 µg/dose or 2 to 6 µg/dose, by a titer, such as 7.3 $\log_{10}HAID_{50}$/dose or 7.3-8.6 $\log_{10}HAID_{50}$/dose, administering the entire dose either can be performed in a single administration or alternatively, in multiple administrations over an interval of 3 hours or less. In particular embodiments, a vaccine dose is orally administered to the animal subject in a single administration, all at one time.

As used herein a "single-dose vaccine" is a vaccine (or multivalent vaccine) comprising at least one immunogen from a pathogen in which the vaccine (or multivalent vaccine) that is administered to an animal in a single administration, or alternatively, in multiple administrations over a short period of time, i.e., over an interval of 3 hours or less, and still aid in the protection of (and/or provide effective protection to) the animal from the pathogen for at least six (6) months, without the need of administering a second dose of the vaccine (e.g., a booster vaccine). In particular embodiments of this type, a single-dose vaccine is orally administered as a single aliquot of the vaccine to an animal subject, e.g., a canine, all in a single administration. In particular embodiments, the single dose vaccine is orally administered in a one (1) mL dose to the animal subject. Accordingly, it is contemplated that a vaccine of the present invention may be orally administered to the animal subject, e.g., a canine, as a single-dose vaccine, for which the duration of immunity is at least 6 months. In certain embodiments, the duration of immunity is at least 9 months. In other embodiments, the duration of immunity is at least 12 months. In still other embodiments, the duration of immunity is at least 18 months.

In alternative aspects, a second dose of a vaccine (or multivalent vaccine) is administered one (1) week, multiple weeks, or months following the primary administration over a 6 to 18-month duration after the administration of the initial oral dose. A booster vaccine can be administered by injection (e.g., intramuscularly, subcutaneously), intranasally, or orally. Accordingly, in some embodiments, the vaccine is orally administered in at least two (2) doses. In some such embodiments, for example, the vaccine is administered twice, with the second dose (e.g., a booster vaccine) being administered at least about 2 weeks after the first. In some embodiments, the vaccine is administered twice, with the second dose being administered no greater than 8 weeks after the first. In other embodiments, the second dose is administered from about 2 weeks to about 4 months after the first dose, from about 2 to about 8 weeks after the first dose, or from about 3 weeks to about 4 weeks after the first dose. In some embodiments, the second dose is administered about 4 weeks after the first dose. The first and subsequent dosages may vary, such as, for example, in amount and/or form. Often, however, the dosages are the same with respect to the amount and form. Whether the administration is performed as a single dose vaccine or in multiple doses [i.e., booster vaccine(s)], it should be understood that subsequent administrations of the vaccine are likely to be needed to be provided to a given animal subject after the 6 to 18 month duration of immunity (or even longer), such as in a yearly or every other year administration regimen.

When a single dose of an oral vaccine of the present invention is sufficient to aid in the protection of (and/or provide effective protection to) the animal from the pathogen for at least six (6) months, the quantity of the antigen(s) in that dose generally comprises a therapeutically effective amount of the vaccine for the 6 month or longer duration. On the other hand, when a booster vaccine dose is required to supplement that initial dose, the combined quantity of the initial vaccine and the booster vaccine may constitute the therapeutically effective amount.

The terms "adjuvant" and "immune stimulant" are used interchangeably herein and are defined as one or more substances that cause stimulation of the immune system.

As used herein, a "non-adjuvanted vaccine" is a vaccine or a multivalent vaccine that does not contain an adjuvant.

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient animal, e.g., a canine.

In specific embodiments, a vaccine of the present invention also may be administered with a pharmaceutically acceptable immune stimulant and/or adjuvant and/or bioadhesive polymer. In this context, an adjuvant is used to enhance an immune response to one or more vaccine antigens/isolates. Accordingly, "adjuvants" are agents that non-specifically increase an immune response to a particular antigen, thus reducing the quantity of antigen necessary in any given vaccine, and/or the frequency of injection necessary in order to generate an adequate immune response to the antigen of interest. Suitable adjuvants for the vaccination of animals include, but are not limited to, mineral gels, such as aluminum hydroxide, aluminum phosphate and alum; surfactants, such as pluronic polyols, and oil emulsions. One adjuvant exemplified below, CARBIGEN™, is a terminally sterilized, carbomer-based (CARBOPOL®934P) adjuvant suspension containing an emulsified component and is free of animal origin ingredients obtained from MVP Adjuvants [located on 4805 "G" Street Omaha, NE]. CARBOPOL®934P is an acrylic acid homopolymer cross-linked with allyl sucrose or allyl pentaerythritol. PVP-K60, a bio-adhesive polymer, is a hygroscopic, amorphous polyvinylpyrrolidone linear nonionic polymer, which is soluble in water and organic solvents, and is pH stable (K60 refers to its molecular weight).

Information concerning adjuvants and various aspects of immunoassays are disclosed, e.g., in the series by P. Tijssen, *Practice and Theory of Enzyme Immunoassays,* 3rd Edition, 1987, Elsevier, New York, incorporated by reference herein. Pharmaceutically acceptable immune stimulants, include bacterial and/or fungal cell wall components (e.g., lipopolysaccharides, lipoproteins, glycoproteins, muramylpeptides), mucoadhesive polymers, various complex carbohydrates derived from plants (e.g., glycans, acemannan), various proteins and peptides derived from animals (e.g., hormones, cytokines, co-stimulatory factors), and novel nucleic acids derived from viruses and/or other sources (e.g., double stranded RNA, CpG).

Live attenuated CPI viruses for use in the vaccines of the present invention may be prepared by conventional means. Conventional means generally include, for example, modifying pathogenic strains by in vitro passaging, cold adaptation, modifying the pathogenicity of the organism by genetic manipulation, selecting non-virulent wild type strains, and other methods well known to the skilled artisan. Such attenuated CPI viruses can then be tested to determine whether they are appropriate for oral administration as detailed in the examples below.

A live modified CPI virus strain can be derived by serial passage of the wild-type virus through cell culture. In alternative embodiments, the live modified CPI virus strain is derived by serial passage of the wild-type virus through a laboratory animal and/or non-host animals. The accumulation of genetic mutation during such passage(s) typically leads to progressive loss of virulence of the organism to the original host. In some embodiments, the live attenuated virus strain is prepared by cold adaptation. A cold-adapted virus has an advantage of replicating only at the temperature found in the upper respiratory tract. A method of generation of a cold-adapted equine influenza virus has been described in U.S. Pat. No. 6,177,082 [hereby incorporated by reference in its entirety]. A desired resulting cold-adapted virus confers one or more of the following phenotypes: cold adaptation, temperature sensitivity, dominant interference, and/or attenuation. In addition, both modified live canine parainfluenza viruses and avirulent live *B. bronchiseptica* have been previously disclosed and are included in commercially available canine vaccines.

Biological Deposit

Cultures of the following biological material have been deposited with the following international depository: American Type Culture Collection (ATCC) 10801 University Boulevard, Manassas, Va. 20110-2209, U.S.A., under conditions that satisfy the requirements of the Budapest Treaty. All restrictions imposed by the depositor on the availability to the public of the deposited material will be irrevocably removed upon granting of a patent.

| Organism | Accession No. | Date of Deposit |
|---|---|---|
| Modified live Canine Parainfluenza Virus | PTA-126273 | Dec. 5, 2019 |
| Attenuated live *Bordetella bronchiseptica* B-C2 | PTA-126272 | Dec. 5, 2019 |

The following examples serve to provide further appreciation of the invention, but are not meant in any way to restrict the effective scope of the invention.

EXAMPLES

Example 1

Efficacy of an Oral Canine Parainfluenza Virus and *B. Bronchiseptica* Vaccine Administered with and without a Bio-Adhesive Polymer or Bio-Adhesive Adjuvant

Materials and Methods

Vaccine:

The experimental vaccines contained avirulent live *B. bronchiseptica* antigen B-C2, ATCC accession No. PTA-126272 and modified live CPI virus, strain Cornell, antigen ATCC accession No. PTA-126273, that was blended with stabilizer solution [hydrolyzed gelatin, N-Z Amine AS (an enzymatic hydrolysate of casein obtained from Millipore Sigma, Burlington, MA), Sorbitol-d, Sodium phosphate dibasic] and then freeze dried. Vaccines that were administered to dogs in Treatment Groups A, C, and D contained 10-15% CARBIGEN™ as an adjuvant. The vaccine administered to the dogs in Treatment Group C also contained the bio-adhesive polymer, PVP-K60.

The titer of the CPI virus of the vaccines varied from 7.5-8.5 $log_{10}HAID_{50}$/mL, whereas the titer of the *B. bronchiseptica* of the vaccines varied from $9.2 \times 10^9$-$1.4 \times 10^{10}$ cfu/mL. All vaccines were freeze dried in vials, and on the day of vaccination, the lyophilized vaccine in each vial was rehydrated with 1 mL of sterile water and like preparations were pooled. The titer of the CPI virus is provided in $log_{10}HAID_{50}$/mL, which is a unit commonly used to estimate the concentration of virus in a sample as calculated by the Spearman-Karber method.

Animals:

Seven, 10-week old Beagles (Marshall Bioresources) were housed communally in a BSL-2 facility on concrete floors covered with wood shavings. Food and water were available ad libitum.

Vaccination and Collection of Serum

On study day 0, dogs in Treatment Group D were vaccinated by the oral route, with a 1 mL dose of vaccine consisting of CPI virus, *B. bronchiseptica* (Bb), and 15% CARBIGEN™. A spray apparatus was attached to a syringe to deliver the vaccine to the back of the throat. On study day 14, all the dogs were vaccinated via the oral route with their respective pooled vaccine [see, Table 1 below]. Whole blood was collected on study day 27 by venipuncture of the jugular vein. The serum was separated by centrifugation and stored at $-10°$ C. or colder until tested.

Detection of CPI Virus Neutralizing Antibodies:

CPI virus neutralizing antibodies were detected using a standard serum neutralization (SN) assay. Serum dilutions were incubated with the CPI virus vaccine strain and inoculated onto dog kidney cells. After 5-7 days, monolayers were fixed and stained with fluorescein-conjugated CPI virus antiserum, and SN antibody titers were calculated as the reciprocal of the serum dilution causing 50% inhibition of virus infection.

TABLE 1

| STUDY DESIGN | | | | | |
|---|---|---|---|---|---|
| Treatment Group | No. of Animals | Vaccine | Dose | Route | Vaccination Day |
| A | 7 | Bb + CPI virus + 15% CARBIGEN ™ | 1.0 mL | Oral | 14 |
| B | 7 | Bb + CPI virus | | | 14 |
| C | 7 | Bb + CPI virus + 10% CARBIGEN ™ + PVP-K60 | | | 14 |
| D | 7 | Bb + CPI virus + 15% CARBIGEN ™ | | | 0 and 14 |
| E | 7 | Placebo-vaccinated controls | | | 14 |

Challenge:

On study day 28, dogs were challenged with a virulent CPI virus.

Post-Challenge Observations and Samples:

Clinical observations were recorded for 11 days post-challenge, and nasal swabs were collected daily for 11 days post-challenge.

Results

Serology:

Prior to vaccination, all the dogs had CPI virus serum neutralization titers less than 2, indicating the dogs were naïve at the time of vaccination. The placebo-vaccinated control dogs remained seronegative (SN<2) just prior to challenge. Nearly all the dogs in each treatment group seroconverted (titer>4) following vaccination [See, Table 2 below].

TABLE 2

SERUM ANTIBODY TITERS TO CPI VIRUS

| Treatment Group | No. of Dogs That Seroconverted on Study Day 27 (Titer Range) |
|---|---|
| A<br>Bb + CPI virus +<br>15% CARBIGEN ™ | 6/7<br>(19->362) |
| B<br>Bb + CPI virus | 6/7<br>(16->256) |
| C<br>Bb + CPI virus +<br>10% CARBIGEN ™ +<br>PVP-K60 | 6/7<br>(38-152) |
| D<br>Bb + CPI virus +<br>15% CARBIGEN ™<br>2 vaccinations | 7/7<br>(32-256) |
| E<br>Placebo-vaccinated controls | 0/7 |

CPI Virus Shedding:

Duration of CPI viral shedding was the primary variable to evaluate vaccine efficacy. The duration of viral shedding from first to last occurrence, in days, for each animal was calculated, and the mean duration of shedding was determined for each treatment group. The mean duration of viral shedding for the placebo-vaccinated control group was 7 days. In contrast, the mean duration of shedding for Treatment Groups A and C was 0 days, while the mean duration of shedding for Treatment Groups B and D was 1 day [see, Table 3 below].

TABLE 3

DURATION OF SHEDDING

| Treatment Group | Mean Duration of Viral Shedding in Days |
|---|---|
| A<br>Bb + CPI virus +<br>15% CARBIGEN ™ | 1 |
| B<br>Bb + CPI virus | 1 |
| C<br>Bb + CPI virus +<br>10% CARBIGEN ™ +<br>PVP-K60 | 0 |
| D<br>Bb + CPI virus +<br>15% CARBIGEN ™<br>2 vaccinations | 1 |
| E<br>Placebo-vaccinated controls | 7 |

These results indicate that the CARBIGEN™ and PVP-K60 had no significant effect on the duration of CPI viral shedding in the vaccine dogs.

Example 2

Dose Response of the Cpi Virus of the Multivalent Oral Cpi Virus and *B. Bronchiseptica* Vaccine with and without Adjuvant

Materials and Methods

Vaccine:

The experimental vaccines contained avirulent live *B. bronchiseptica* antigen B-C2 ATCC accession No.

PTA-126272 and modified live CPI virus, strain Cornell, antigen ATCC accession No. PTA-126273, that was blended with stabilizer [hydrolyzed gelatin, N-Z Amine AS, Sorbitol-d, Sodium phosphate dibasic] and then freeze dried. Vaccines that were administered to dogs in Treatment Groups C and D contained 15% CARBIGEN™ as an adjuvant. On the day of vaccination, each vial of lyophilized vaccine was rehydrated with 1 mL of sterile water, and like preparations were pooled. The titer of the CPI virus in the vaccines used in Treatment Groups A-D was 8.6, 7.3, 7.6, and 6.3 $\log_{10}\text{HAID}_{50}/\text{mL}$, respectively, as denoted in Table 5.

Animals:

Fifteen, 17-week old Beagles (Marshall Bioresources) were housed communally in a BSL-2 facility on concrete floors covered with wood shavings. Food and water were available ad libitum.

Vaccination and Collection of Serum

On study day 0, the dogs were vaccinated by the oral route with a 1 mL dose of their respective pooled vaccine [see, Table 4 below]. A spray apparatus was attached to a syringe to deliver the vaccine to the back of the throat. Whole blood was collected on study day 27 by venipuncture of the jugular vein. The serum was separated by centrifugation and stored at −10° C. or colder until tested.

Detection of CPI Virus Neutralizing Antibodies:

CPI virus neutralizing antibodies were detected using a standard SN assay. Serum dilutions were incubated with CPI virus vaccine strain and inoculated onto dog kidney cells. After 5-7 days, monolayers were fixed and stained with fluorescein-conjugated CPI virus antiserum, and SN antibody titers were calculated as the reciprocal of the serum dilution causing 50% inhibition of virus infection.

Challenge:

On study day 28, dogs were challenged with virulent CPI virus.

Post-Challenge Observations and Samples:

Clinical observations were recorded for 14 consecutive days, and nasal swabs were collected for 10 consecutive days post-challenge.

TABLE 4

STUDY DESIGN

| Treatment Group | No. of Animals | Vaccine | Dose | Route | Vaccination Day |
|---|---|---|---|---|---|
| A | 6 | CPI virus<br>(8.0 $\log_{10}\text{HAID}_{50}/\text{mL}$) +<br>*B. bronchiseptica* | 1.0 mL | Oral | Study Day 0 |
| B | 6 | CPI virus<br>(6.5 $\log_{10}\text{HAID}_{50}/\text{mL}$) +<br>*B. bronchiseptica* | | | |
| C | 6 | CPI virus<br>(8.0 $\log_{10}\text{HAID}_{50}/\text{mL}$) +<br>*B. bronchiseptica* with<br>15% CARBIGEN ™ | | | |
| D | 6 | CPI virus<br>(6.5 $\log_{10}\text{HAID}_{50}/\text{mL}$) +<br>*B. bronchiseptica* with<br>15% CARBIGEN ™ | | | |
| E | 6 | Placebo-vaccinated controls | | | |

Results

Serology

Prior to vaccination, all dogs had CPI virus serum neutralization titers less than 2, indicating that the dogs were naïve at the time of vaccination. The placebo-vaccinated control dogs remained seronegative (SN<2) just prior to challenge. Nearly all the dogs in each treatment group seroconverted (titer>4) following vaccination [see, Table 5 below].

TABLE 5

| SERUM ANTIBODY TITERS TO CPI VIRUS | |
|---|---|
| Treatment Group | No. of Dogs That Seroconverted on Study Day 27 (Titer Range) |
| A CPI virus (8.6 $\log_{10}HAID_{50}/mL$) + *B. bronchiseptica* | 6/6 (19-431) |
| B CPI virus (7.3 $\log_{10}HAID_{50}/mL$) + *B. bronchiseptica* | 6/6 (7-91) |
| C CPI virus (7.6 $\log_{10}HAID_{50}/mL$) + *B. bronchiseptica* with 15% CARBIGEN ™ | 6/6 (7-215) |
| D CPI virus (6.3 $\log_{10}HAID_{50}/mL$) + *B. bronchiseptica* with 15% CARBIGEN ™ | 2/6 (7-256) |
| E Placebo-vaccinated controls | 0/7 |

CPI Virus Shedding:

Duration of CPI viral shedding was the primary variable to evaluate vaccine efficacy. The duration of viral shedding from first to last occurrence, in days, for each animal was calculated, and the mean duration of shedding was determined for each treatment group. All the placebo-vaccinated control dogs (Treatment Group E) shed virus, and the mean duration of shedding was 6 days. In contrast, the mean duration of shedding for Treatment Groups A-D was 1, 0, 1, and 5, respectively [see, Table 6 below].

TABLE 6

| DURATION OF SHEDDING | |
|---|---|
| Treatment Group | Mean Duration of Viral Shedding in Days |
| A CPI virus (8.6 $\log_{10}HAID_{50}/mL$) + *B. bronchiseptica* | 1 |
| B CPI virus (7.3 $\log_{10}HAID_{50}/mL$) + *B. bronchiseptica* | 2 |
| C CPI virus (7.6 $\log_{10}HAID_{50}/mL$) + *B. bronchiseptica* with 15% CARBIGEN ™ | 1 |

TABLE 6-continued

| DURATION OF SHEDDING | |
|---|---|
| Treatment Group | Mean Duration of Viral Shedding in Days |
| D CPI virus (6.3 $\log_{10}HAID_{50}/mL$) + *B. bronchiseptica* with 15% CARBIGEN ™ | 5 |
| E Placebo-vaccinated controls | 6 |

These results suggest that $\geq 6.3$ $\log_{10}HAID_{50}/mL$ of the modified live CPI virus in a 1 mL dose is needed for the oral modified live CPI virus vaccine to be efficacious, as evaluated as a function of the duration of viral shedding.

Example 3

Immunogenicity Study in Dogs to Demonstrate Efficacy of the Cpi Fraction of an Oral Canine Parainfluenza and *Bordetella Bronchiseptica* Combination Vaccine Materials and Methods Vaccine:

The test vaccine consisted of modified live CPI virus strain Cornell, ATCC accession No. PTA-126273 and avirulent live *B. bronchiseptica* antigen B-C2, ATCC accession No. PTA-126272 that was blended with stabilizer [hydrolyzed gelatin, N-Z Amine AS, Sorbitol-d, Sodium phosphate dibasic] and then freeze dried. The placebo vaccine consisted of all the components in the test vaccine except for the CPI antigen. On the day of vaccination, each vial of lyophilized vaccine was rehydrated with 1 mL of sterile water, and like preparations were pooled.

Animals:

Twenty, 7-week old Beagles (Marshall Bioresources) were housed communally in a BSL-2 facility on concrete floors covered with wood shavings, and 19, 7-week old Beagles (Marshall Bioresources) were housed similarly in another room. Food and water were available ad libitum.

Vaccination and Collection of Serum:

On study day 0, the dogs were vaccinated by the oral route with a 1 mL dose of their respective pooled vaccine [see, Table 7 below]. A spray apparatus was attached to a syringe to deliver the vaccine to the back of the oral cavity (oropharynx). Whole blood was collected on study day 21 by venipuncture of the jugular vein. The serum was separated by centrifugation and stored at −10° C. or colder until tested.

Detection of CPI Virus Neutralizing Antibodies:

CPI virus neutralizing antibodies were detected using a standard SN assay. Serum dilutions were incubated with CPI virus vaccine strain and inoculated onto dog kidney cells. After 5-7 days, monolayers were fixed and stained with fluorescein-conjugated CPI virus antiserum, and SN antibody titers were calculated as the reciprocal of the serum dilution causing 50% inhibition of virus infection.

US 12,648,991 B2

Challenge:

On study day 21, dogs were challenged with virulent CPI virus.

Post-Challenge Observations and Samples:

Clinical observations were recorded for 14 consecutive days, and nasal swabs were collected for 10 consecutive days post-challenge.

TABLE 7

STUDY DESIGN

| Treatment Group | No. of Animals | Vaccine | Dose | Route | Vaccination Day |
|---|---|---|---|---|---|
| A | 20 | Test Vaccine CPI + B. bronchiseptica | 1.0 mL | Oral | Study Day 0 |
| B | 19 | Placebo Vaccine B. bronchiseptica | | | |

Results

Serology:

Prior to vaccination, all dogs had CPI virus serum neutralization titers less than 2, indicating that the dogs were naïve at the time of vaccination. Vaccination with the placebo vaccine did not induce antibodies specific to CPI, whereas, vaccination with the test vaccine induced CPI serum neutralization titers of 4 or greater in 15 of 20 (75%) vaccinates, with titers ranging from 6 to 861 (GMT=31) 3 weeks after vaccination [see, Table 8 below].

TABLE 8

CPI SERUM ANTIBODY TITERS

| Treatment Group | No. of Dogs That Seroconverted on Study Day 21 (Titer Range) |
|---|---|
| A Vaccinates | 15/20 (6-861) |
| B Placebo-vaccinated Controls | 0/20 (<2) |

CPI Virus Shedding:

Duration of CPI viral shedding was the primary variable to evaluate vaccine efficacy. The duration of viral shedding from first to last occurrence, in days, for each animal was calculated, and the mean duration of shedding was determined for each treatment group. All but one of the placebo-vaccinated control dogs (Treatment Group B) shed CPI virus (i.e., 95%); whereas, only 11 of the vaccinates shed virus (i.e., 55%). The median duration of CPI viral shedding was 6 days for the placebo-vaccinated control dogs, compared to only a median duration of shedding of 1.5 days for the vaccinated dogs [see, Table 9 below].

TABLE 9

DURATION OF SHEDDING

| Treatment Group | Mean Duration of Viral Shedding in Days |
|---|---|
| A Vaccinates | 1.5* |
| B Placebo-vaccinated Controls | 6 |

*p-value < 0.0001

These results show that 7.1 $\log_{10}HAID_{50}$/mL of CPI virus in a 1 mL dose is sufficient for the oral modified live CPI virus vaccine to be efficacious, as evaluated as a function of the duration of viral shedding.

Example 4

Immunogenicity Study to Demonstrate Efficacy of the *Bordetella Bronchiseptica* Fraction of an Oral Canine Parainfluenza and *Bordetella Bronchiseptica* Combination Vaccine Materials and Methods Vaccine:

The test vaccine consisted of modified live CPI virus strain Cornell, ATCC accession No. PTA-126273 and avirulent live *B. bronchiseptica* antigen B-C2, ATCC accession No. PTA-126272 that was blended with stabilizer [hydrolyzed gelatin, N-Z Amine AS, Sorbitol-d, Sodium phosphate dibasic] and then freeze dried. The placebo vaccine consisted of all the components in the test vaccine except for the *B. bronchiseptica* antigen. On the day of vaccination, each vial of lyophilized vaccine was rehydrated with sterile water, and like preparations were pooled.

Animals:

Twenty-one, 7-week old Beagles were housed communally in a BSL-2 facility on concrete floors covered with wood shavings, and twenty-one, 7-week old Beagles were housed similarly in another room. Food and water were available ad libitum.

Vaccination:

On study day 0, the dogs were vaccinated by the oral route with a 1 mL dose of their respective pooled vaccine [see, Table 10 below]. A spray apparatus was attached to a syringe to deliver the vaccine to the back of the oral cavity (oropharynx).

Sample Collection:

On study day 34, whole blood was collected by venipuncture of the jugular vein. The serum was separated by centrifugation and stored at −10° C. or colder until tested. Nasal swabs were also collected on study day 34 to test for the presence of *B. bronchiseptica*. Once collected, swabs were placed in whirl pack bags and tested immediately.

Detection of *B. bronchiseptica* Agglutinating Antibodies:

*B. bonchiseptica* antibodies were detected using a standard microagglutination test. Briefly, 2-fold serial dilutions of test serum, known positive serum, and known negative serum were performed in a U-bottom microtiter plate, using normal saline containing 0.1% gelatin as the diluent. *B. bronchiseptica* antigen (100 μL) was added to each well and mixed for 15-30 seconds on a microtiter plate mixer. The plates were incubated at 36±2° C. for 1-3 hours and then incubated at 2-7° C. for 36-72 hours. The plates were read visually for agglutination, and the titers were expressed as the reciprocal of the highest dilution showing complete agglutination.

Challenge:

On study day 35, dogs were challenged with virulent *B. bronchiseptica*.

Post-Challenge Observations and Samples:

Dogs were observed for at least 30 minutes twice daily for 28 days post-challenge for clinical signs including, but not limited to, nasal discharge, dyspnea, depression, and coughing. Nasal swabs were collected on study days 42, 45, 49, 52, 58, and 63 to determine shedding of challenge organisms.

TABLE 10

STUDY DESIGN

| Treatment Group | No. of Animals | Vaccine | Dose | Route | Vaccination Day |
|---|---|---|---|---|---|
| A | 20 | Test Vaccine *B. bronchiseptica* + CPI | 1.0 mL | Oral | Study Day 0 |
| B | 19 | Placebo Vaccine CPI | | | |

Results

Serology:

Prior to vaccination, all dogs had low antibody titers (≤4) to *B. bronchiseptica*, indicating that the dogs were naïve at the time of vaccination. Vaccination with the test vaccine induced *B. bronchiseptica* agglutination titers in 20 of the 21 dogs, with a range of 16 to 128 on study day 34; GMT=<39. In contrast, the antibody titers in all the placebo-vaccinated control dogs remained low with a range of <2 to 8; GMT=<1 [see, Table 11 below].

TABLE 11

*B. BRONCHISEPTICA* SERUM ANTIBODY TITERS

| Treatment Group | No. of Dogs That Seroconverted on Study Day 34 (Titer Range) |
|---|---|
| A Vaccinates | 20/21 (16-128) |
| B Placebo-vaccinated Controls | 0/21 (<2-8) |

Clinical Signs Post-Challenge:

Following challenge, all the placebo-vaccinated control dogs developed clinical signs associated with a *B. bronchiseptica* infection, specifically spontaneous coughing. An affected dog was defined as having spontaneous coughing or spontaneous coughing with retching on 2 or more consecutive days during the post-challenge observation period. All 20 placebo-vaccinated control dogs were affected compared to only 9 of the 21 (43%) vaccinated dogs; p-value<0.0001 [see, Table 12 below]. In addition, none of the vaccinates coughed for two consecutive days more than once during the post-challenge observation period, whereas 18 of the 20 (90%) placebo-vaccinated controls coughed on two consecutive days 2-13 times.

TABLE 12

SUMMARY OF AFFECTED DOGS

| Treatment Group | Total Number of Dogs |
|---|---|
| A Vaccinates | 9/21 (43%)* |
| B Placebo-Vaccinated Controls | 20/20 (100%) |

*p-value < 0.0001

The number of days that a dog spontaneously coughed during the 28-day post-challenge observation period also was analyzed. The mean number of days that dogs in Treatment Group B spontaneously coughed was 16.6 days compared to only 3.5 days for dogs in Treatment Group A; p-value<0.0001 [see, Table 13 below].

TABLE 13

SUMMARY OF COUGHING

| Treatment Group | Total Number of Dogs |
|---|---|
| A Vaccinates | (3.5%)* |
| B Placebo-Vaccinated Controls | (16.6%) |

*p-value < 0.0001

*B. bronchiseptica* Shedding:

Nasal swabs were collected twice a week for 4 weeks post-challenge to determine shedding of challenge organisms. On study day 42, there was no difference in bacterial shedding between the placebo-vaccinated control group and the vaccine group. However, by study day 45, the placebo vaccinated control group was shedding 38,141 cfu/mL of *B. bronchiseptica*, whereas the vaccinate group was shedding only 1,523 cfu/mL. The bacterial shedding in the placebo-vaccinated control group peaked at 16 days post-challenge (study day 52) with 75,293 cfu/mL. In contrast, bacterial shedding in the vaccinated group peaked at 6 days post-challenge (study day 42) with only 4,173 cfu/mL. Bacterial counts continued to decline in the vaccinated dogs until the end of the study. By study day 63, the bacterial shedding in the vaccinated group was only 6 cfu/mL, whereas, the bacterial shedding remained elevated within the placebo-vaccinated control group at 35,400 cfu/mL.

These data demonstrate a dramatic reduction in the ability of *B. bronchiseptica* to colonize within the nasal mucosa of the vaccinate group. The overall mean bacterial shedding for the placebo-vaccinated controls and vaccinates was 37,035 cfu/mL and 849 cfu/mL, respectively [see, Table 14 below], and the amount of *B. bronchiseptica* shed on each collection day was statistically lower in the vaccinated dogs than in the placebo-vaccinated control dogs; p-value s 0.0001.

TABLE 14

| | | | | *B. BRONCHISEPTICA* ORGANISMS ISOLATED FROM NASAL SWABS POST-CHALLENGE (CFU/ML) | | | | | |
| Treatment Group | Day 34* | Day 42 | Day 45 | Day 49 | Day 52 | Day 55 | Day 58 | Day 63 | Overall Mean |
|---|---|---|---|---|---|---|---|---|---|
| Vaccinates | 0 | 4,173* | 1,523** | 253** | 751** | 33** | 50** | 6** | 849 |
| Controls | 0 | 5,235 | 38,141 | 70,390 | 75,293 | 35,638 | 36,183 | 35,400 | 37,035 |

*p-value = 0.0001
**p-value < 0.0001

These results show that $3.9 \times 10^8$ cfu/mL of *B. bronchiseptica* avirulent strain B-C2, ATCC accession No. PTA-126272, in a 1 mL dose is sufficient for the oral vaccine to be efficacious, as evaluated by the number of dogs that had spontaneous coughing or spontaneous coughing with retching on two or more consecutive days during the post-challenge observation period.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

We claim:

1. An oral bivalent vaccine for providing effective protection to a canine from upper respiratory diseases and infectious tracheobronchitis, the oral bivalent vaccine consisting essentially of a modified live canine parainfluenza (CPI) virus and an avirulent live *Bordetella bronchiseptica* (*B. bronchiseptica*) and optionally an adjuvant, and wherein the oral bivalent vaccine is formulated for oral administration.

2. The oral bivalent vaccine of claim 1, wherein the titer of the avirulent live *B. bronchiseptica* in the vaccine is about $1 \times 10^7$ cfu/mL to about $1 \times 10^{12}$ cfu/mL.

3. The oral bivalent vaccine of claim 1, wherein the modified live CPI virus has the ATCC accession No. PTA-126273.

4. The oral bivalent vaccine of claim 1, wherein the avirulent live *B. bronchiseptica* has the ATCC accession No. PTA-126272.

5. The oral bivalent vaccine of claim 1, wherein the vaccine is a single-dose oral vaccine.

6. The oral bivalent vaccine of claim 1, wherein the vaccine does not comprise an adjuvant.

7. The oral bivalent vaccine of claim 1, wherein the vaccine comprises an adjuvant.

8. The oral bivalent vaccine of claim 1, wherein the vaccine is formulated for oral administration in a single-dose volume of about 0.2 mL to about 5 mL.

9. The oral bivalent vaccine of claim 1, wherein a single dose of the oral vaccine provides effective protection to a canine from upper respiratory diseases and infectious tracheobronchitis for at least 12 months upon administration.

10. The oral bivalent vaccine of claim 1, wherein the oral vaccine is lyophilized.

* * * * *